United States Patent
Graham

(10) Patent No.: US 7,384,918 B2
(45) Date of Patent: *Jun. 10, 2008

(54) BOTULINUM TOXIN FOR TREATING MUSCLE CONTRACTURE

(75) Inventor: Herbert Kerr Graham, Victoria (AU)

(73) Assignee: Allergan, Inc., Irvine, CA (US)

( * ) Notice: Subject to any disclaimer, the term of this patent is extended or adjusted under 35 U.S.C. 154(b) by 215 days.

This patent is subject to a terminal disclaimer.

(21) Appl. No.: 11/209,304

(22) Filed: Aug. 22, 2005

(65) Prior Publication Data

US 2006/0093624 A1    May 4, 2006

Related U.S. Application Data

(63) Continuation-in-part of application No. 10/104,899, filed on Mar. 22, 2002, now Pat. No. 6,939,852, which is a continuation-in-part of application No. 08/211,352, filed as application No. PCT/GB92/01697 on Sep. 16, 1992, now Pat. No. 6,395,277.

(30) Foreign Application Priority Data

Sep. 24, 1991 (GB) .................................. 9120306.7

(51) Int. Cl.
*A61K 38/00* (2006.01)
*A61K 39/00* (2006.01)
*C07K 14/33* (2006.01)

(52) U.S. Cl. ........................ 514/21; 514/12; 424/184.1; 424/236.1; 424/247.1; 530/350; 604/51

(58) Field of Classification Search .................. 514/21, 514/12; 424/184.1, 236.1, 247.1; 530/350; 604/51

See application file for complete search history.

(56) References Cited

U.S. PATENT DOCUMENTS

| 4,932,936 | A | 6/1990 | Dykstra et al. |
| 5,053,005 | A | 10/1991 | Borodic |
| 5,298,019 | A | 3/1994 | Borodic |
| 6,395,277 | B1 | 5/2002 | Graham |
| 6,448,231 | B2 | 9/2002 | Graham |
| 6,939,852 | B2 * | 9/2005 | Graham .................. 514/12 |

FOREIGN PATENT DOCUMENTS

DE           19852981           5/2000

OTHER PUBLICATIONS

Bodde H.E., et al., Transdermal Peptide Delivery, Biochem Soc Trans 17(5); 943-5: 1989.
Botulinum toxin may be useful in range of muscular disorders, Int Med News Aug. 15, 1991;24(16):36 Author unknown (Abstract).
Brin, M., et al., Assessment: The clinical usefulness of botulinum toxin-A in treating neurologic disorders, Neurology 1990;40:1332-1336.
Choi, H-K, et al., Transdermal delivery of bioactive peptides: the effect of n-decylmethyl sulfoxide, pH, and inhibitors on Enkephalin metabolism and transport, Pharm Res 7(11):1099-1106 (1990).
Cioffi, G.A., et al., Microvasculature of the Anterior Optic Nerve, Survey of Ophthalmology, vol. 38, Suppl., May 1994.
Consensus Conference, Clinical Use of Botulinum Toxin, Connecticut Medicine, vol. 55, No. 8, pp. 471-477 (1991).
Clinical Use of Botulinum Toxin, NIH Consens Statement, Nov. 12-14, 1990; 8(8):1-20.
Cosgrove et al., Botulinum toxin A prevents the development of contractures in the hereditary spastic mouse model, Dev Med and Child Neurol. 1994, 36, 379-385.
Cosgrove et al., Botulinum toxin in the management of lower limb in cerebral palsy, Dev Med and Child Neurol. 1994, 36, 386-396.
Das, T.K., et al. Effect of treatment with botulinum toxin on spasticity, Postgraduate Medical Journal (1989) 65,208-210.
Duane, D.D., Spasmodic Torticollis, In: Jankovic J., ed., Advances in Neurology, vol. 49, Facial Dyskinesias, NY, Raven Press; 1988:pp. 135-150 (Abstract).
Dunn, W.J., et al., Botulinum Toxin for the Treatment of Dysthyroid Ocular Myopathy, Ophthalmology, vol. 93, No. 4, Apr. 1986, pp. 470-475.
Hatheway, C.L., Bacterial Sources of Clostridial Neurotoxins, Chapter 1, pp. 3-24, L.L. Simpson, editor, Botulinum Neurotoxin and Tetanus Toxin, Academic Press, Inc. 1989.
Jankovic, J. et al., Therapeutic Uses of Botulinum Toxin, The New England Journal of Medicine, vol. 324, Apr. 25, 1991, No. 17, pp. 1186-1194.
Liedtke, R.K., et al., Transdermal administration of insulin in type II diabetes, Results of a clinical pilot study; Arneimittelforschung 40(8); 884-6:1990 (German) (English abstract).
Overmyer, R.H., Botulinum toxin: poison with a purpose, Mod Med Sep. 1991;59:112-6 (Abstract).
Park et al., Binding of *Clostridium botulinum* type B toxin to rat brain synaptosome, Fems Microbiol Lett., 1990; 60(3):243-7. (Abstract).
Rosenbaum, A.L., et al., Vertical rectus muscle transposition and botulinum toxin (Oculinum) to medial rectus for abducens palsy, Arch Ophthalmol Jun. 1989; 107(6):820-3, (Abstract).
Sanders, L.M., Drug delivery systems and routs of admnistration of peptide and protein drugs, Eur J of Drug Metabolism and Pharmacokinetics, 1990, vol. 12, No. 2, pp. 95-102.
Sasaki, H. et al., Effect of pyrrolidone derivatives on lipid membrane and protein conformation as transdermal penetration enhancer, J. Pharmacobio-Dyn., 13; 468-474: 1990.
Sato et al., Purification and some properties of a proteinase and an esterase released from *Clostridium botulinum* A, B, and F types, Nippon Saikingaku Zasshi 1973; 28(4):367-74. (Abstract Only).

(Continued)

*Primary Examiner*—Jon P Weber
*Assistant Examiner*—Abdel A Mohamed
(74) *Attorney, Agent, or Firm*—Claude L. Nassif; Stephen Donovan; Martin A. Voet

(57) ABSTRACT

The invention provides for the use of a botulinum toxin to treat contracture, such as muscle contracture, in patients by transdermal administration of the botulinum toxin.

12 Claims, No Drawings

OTHER PUBLICATIONS

Schwartz, B., Circulatory Defects of the Optic Disk and Retina in Ocular Hpertension and High Pressure Open-Angle Glaucoma, Survey of Ophthalmology, vol. 38, Suppl. May 1994.

Scott, A.B., et al., Botulinum Toxin Injection in the Management of Lateral Rectus Paresis, Ophthalmology, vol. 92, No. 5, May 1985, pp. 676-683.

Snow, B.J., et al., Treatment of Spasticity with Botulinum Toxin: A Double-Blind Study, Annals of Neurology, vol. 28, No. 4, Oct. 1990, pp. 512-515.

Srinivasan, V., et al., Iontophoresis of polypeptides: effect of ethanol pretreatment of human skin, J. Pharm Sci 79(7), Jul. 1990.

Tonnesen, P., et al., A double blind trial of a 16-hour transdermal nicotine patch in smoking cessation, New Eng J Medicine, 325(5); 311-315:Aug. 1991.

Verhoef, J.C., et al., Transport of peptide and protein drugs across biological membranes, Eur J Drug Metab Pharmacokinet Apr.-Jun. 1990, 15(2):83-93.

Wright, James, et al, *The Spastic Mouse and the search for an animal model of spasticity in human beings*, Clinical Orthrop. and Related Research, Apr. 1990, No. 253, pp. 12-19.

\* cited by examiner

BOTULINUM TOXIN FOR TREATING MUSCLE CONTRACTURE

CROSS REFERENCE TO RELATED APPLICATIONS

This application is a continuation in part of U.S. application Ser. No. 10/104,899, filed Mar. 22, 2002, now U.S. Pat. No. 6,939,852, issued Sep. 6, 2005, which is a continuation in part of U.S. application Ser. No. 08/211,352, filed Jun. 27, 1994, now U.S. Pat. No. 6,395,277, which is a section 371 application from PCT/GB92/01697, filed Sep. 16, 1992, which claims priority to GB 9120306.7, filed Sep. 24, 1991, the entire contents of which are hereby incorporated by reference.

BACKGROUND

The present invention relates to the treatment of contracture in a patient and in particular to the treatment of muscle contractures by administration of a Clostridial neurotoxin, such as a botulinum toxin.

Contracture refers to a condition of a patient associated with permanent tightening of non-bony tissues, such as muscles, tendons, ligaments, and skin. The permanent tightening prevents normal movement of one or more body parts associated with the contracture. The contracture can cause permanent deformities in patients with contractures.

Muscle contracture refers to a persistent and involuntary muscle shortening. Contracture is associated with conditions such as Dupuytren's contracture, claw hand, food drop, wrist drop, Volkmann's contracture, Becker's muscular dystrophy, cerebral palsy, Duchenne's muscular dystrophy, and back pain.

Dupuytren's contracture is a thickening and contracture of tissue beneath the skin on the palm of the hand and fingers of a patient.

Volkmann's ischemic contracture is a deformity of the hand, fingers, and wrist caused by injury to the muscles of the forearm. Swelling resulting from an injury to the forearm can cause a decreased blood flow (e.g., ischemia) to the forearm. Prolonged decreased blood flow can result in injury to nerves and muscles, causing them to become shortened and stiff, and thereby causes a bending of a joint that cannot be straightened.

Becker's muscular dystrophy is an inherited disorder characterized by slowly progressive muscle weakness of the legs and pelvis. Muscle contractures occur in the legs and heels resulting from a shortening of muscle fibers and fibrosis of connective tissues. The muscle contractures can result in bone deformities.

Duchenne muscular dystrophy is an inherited disorder associated with a rapidly progressive muscle weakness that begins in the legs and pelvis and can affect the whole body of a patient.

Cerebral palsy is a collective name given to a range of conditions caused by brain injury caused at or around the time of birth, or in the first year of an infant's life. The brain injury may be caused, for example, by trauma during delivery. It may also arise through such causes as trauma due to road traffic accidents or meningitis during the first year of life. It has been found that there is an increased risk of cerebral palsy in prematurely born babies and, as a result of the improvements in technology which enable premature babies to be kept alive from a much earlier age, the incidence of cerebral palsy in many countries is actually increasing rather than falling.

Although the brain injury causing cerebral palsy is a non-progressive injury, its effects may change as the sufferer grows older. Cerebral palsy can be classified as spastic, dyskinetic, ataxic, and mixed. The largest group of sufferers from cerebral palsy suffer from spastic cerebral palsy. Spastic cerebral palsy is characterized by dynamic contractures of the muscles which impair or inhibit completely the sufferer's ability to use his or her muscles. Moreover, muscle growth is impaired such that the longitudinal muscles become shorter relative to their associated bones as the infant grows older. Where the leg muscles are affected, the mobility of the sufferer can be severely reduced. Conventional attempts to cure this defect and to restore a measure of normal mobility typically have involved surgical intervention to alter the lengths of the tendons once the state has been reached at which the knee joint can no longer be straightened or the sufferer can only walk on tiptoe. Dyskinetic cerebral palsy involves the development of abnormal movements, such as twisting, jerking, and the like. Ataxic cerebral palsy involves tremors, unsteady gate, loss of coordination, and abnormal movements.

Muscle contracture may also cause back pain by directly impinging on or activating pain nerves within the muscle, compressing an artery and decreasing blood flow to a back area, and/or increasing compression exerted on a vertebral disc.

There remains a need for a treatment for contracture and symptoms associated with contracture which removes or reduces the need to resort to surgical intervention. Moreover, there remains a need for a treatment which can augment surgical intervention to improve the mobility and/or reduce a deformity of the sufferer.

A bacterial toxin, botulinum toxin, has been used in the treatment of a number of conditions involving muscular spasm, for example a blepharospasm, spasmodic torticollis (cervical dystonia), oromandibular dystonia and spasmodic dysphonia (laryngeal dystonia). The toxin binds rapidly and strongly to presynaptic cholinergic nerve terminals and inhibits the exocytosis of acetylcholine by decreasing the frequency of acetylcholine release. This results in paralysis, and hence relaxation, of the muscle afflicted by spasm.

The term botulinum toxin is used herein as a generic term embracing the family of toxins produced by the anaerobic bacterium Clostridium botulinum and, to date, seven immunologically distinct toxins have been identified. These have been given the designations A, B, C, D, E, F and G. For further information concerning the properties of the various botulinum toxins, reference is made to the article by Jankovic & Brin, The New England Journal of Medicine, pp 1186-1194, No. 17, 1991 and to the review by Charles L. Hatheway, Chapter 1 of the book entitled "Botulinum Neurotoxin and Tetanus Toxin" Ed. L. L. Simpson, published by Academic Press Inc., of San Diego, Calif. 1989, the disclosures of which are incorporated herein by reference.

The Jankovic and Brin article reviews the use of botulinum toxin type A by intramuscular injection to treat focal dystonias, strabismus, blepharospasm and other facial nerve disorders, including hemifacial disorders and use with regard to other spastic conditions is also reviewed. The Hatheway publication reviews the properties of botulinum toxin and tetanus toxin and the organisms which produce them, noting on page 5 that subcutaneous injection of the toxin has been carried out.

The neurotoxic component of botulinum toxin has a molecular weight of about 150 kilodaltons and is thought to comprise a short polypeptide chain of about 50 kD which is considered to be responsible for the toxic properties of the toxin, and a larger polypeptide chain of about 100 kD which is believed to be necessary to enable the toxin to penetrate the nerve. The "short" and "long" chains are linked together by means of disulphide bridges.

The neurotoxic polypeptide component is present in a complex with non-toxic proteins and haemagglutinins, the molecular weight of the complex being in the region of 900 kD.

Botulinum toxin is obtained commercially by establishing and growing cultures of C. botulinum in a fermenter and the harvesting and purifying the fermented mixture in accordance with known techniques.

The "A" form of botulinum toxin is currently available commercially from several sources, for example, from Porton Products Ltd., UK under the tradename "DYSPORT®", and from Allergan Inc., Irvine, Calif. under the trade name "BOTOX®."

DESCRIPTION

It has now been found by the present inventor that patients suffering from contracture, such as muscle contracture, can be successfully treated by administration of a botulinum toxin. The administration of the botulinum toxin relieves one or more symptoms associated with the contracture. For example, a contracture patient can be treated with a botulinum toxin to reduce pain associated with the contracture, reduce deformity associated with the contracture, and/or enhance mobility of the contracture patient. In muscle contracture patients, such as patients that are being treated for a muscle contracture, administration of a botulinum toxin can result in improvements in function following treatment with the botulinum toxin, such improvements can persist even when the tone reducing effects of the toxin have worn off.

In one particular situation, children suffering from dynamic muscle contractures associated with cerebral palsy can be successfully be treated with a botulinum toxin. Administering a botulinum toxin to a juvenile muscle contracture patient can effectively reduce the tone of the spastic muscle and cause an increase in longitudinal growth of the muscle relative to a similar muscle that does not receive a botulinum toxin treatment.

In other situations, a patient suffering from a contracture, such as a patient suffering from Dupuytren's contracture, claw hand, food drop, wrist drop, Volkmann's contracture, Becker's muscular dystrophy, cerebral palsy, Duchenne's muscular dystrophy, and back pain, can be successfully treated for prolonged periods of time by administering a botulinum toxin to the patient. Typically, the botulinum toxin will be administered at a site associated with the contracture. In certain situations, the botulinum toxin is administered to treat a muscle contracture.

Thus, in one aspect, the present invention provides a method of treating a muscle contracture of a patient, which method comprises administering to the patient a therapeutically effective amount of substance which blocks the release of synaptic vesicles containing acetylcholine. Administering the substance is effective in relieving the muscle contracture and reducing or eliminating one or more symptoms associated with the muscle contracture. In certain embodiments, the muscle contracture is a dynamic muscle contracture. In additional embodiments, the muscle contracture is a dynamic contracture of one or more muscles of a juvenile patient suffering from arrested muscle growth.

The present invention also provides a method of treating a juvenile patient suffering from cerebral palsy, which method comprises administering to the patient a therapeutically effective amount of substance which blocks the release of synaptic vesicles containing acetylcholine.

In a further aspect the invention provides a method of treating muscle contracture of a patient, which method comprises administering to the patient a therapeutically effective amount of a presynaptic neurotoxin, for example a bacterial neurotoxin such as a botulinum toxin.

In a still further aspect the invention provides a method of treating a juvenile patient suffering from arrested muscle growth due to a cerebral palsy, which method comprises administering a presynaptic neurotoxin (for example a bacterial neurotoxin such as a botulinum toxin) to the patient in a non toxic amount sufficient to reduce muscle tone and promote improved muscle growth.

The botulinum toxin used according to the present invention preferably is Botulinum toxin A. Botulinum toxin A is available commercially from Porton Products Limited, UK, and from Allergan Inc., Irvine, Calif.

For treatment of muscle contracture patients, the toxin is preferably administered in the region of the neuromuscular junction associated the muscle contracture. In certain embodiments, the toxin is administered by intramuscular injection directly into a spastic muscle, in the region of the neuromuscular junction. In other embodiments, other modes of administration, such as sub-cutaneous injection, may be employed where appropriate. In preferred embodiments of the present methods, the toxin is transdermally administered to the patient to treat a muscle contracture. In other words, a method of treating a muscle contracture of a patient comprises transdermally administering the botulinum toxin to the patient to treat the muscle contracture. For example, in certain embodiments, the botulinum toxin is administered to the patient without injecting the botulinum toxin into the patient using a needle.

Muscle contractures, including muscle contractures associated with cerebral palsy, back pain, ischemia, and the like, can be successfully treated by transdermally administering a botulinum toxin to the patient. Transdermal administration of a botulinum toxin allows the toxin to be delivered to a target site associated with a muscle contracture to provide a therapeutic effect, such as a relaxation of the muscle or a decrease in muscle spasticity without the difficulty and discomfort associated with needle injection of the botulinum toxin. If desired, patches containing muscle contracture relieving amounts of a botulinum toxin can be self administered by the patient based on a physician's instructions. Thus, transdermal administration of a botulinum toxin to treat any muscle contracture provides advantages compared to injecting botulinum toxin with a needle.

Muscle contractures that can be treated with transdermal administration of a botulinum toxin can be identified and/or determined by a physician using routine methods known to persons of ordinary skill in the art. For example, a physician can examine a patient for increased muscle activity, such as for persistent involuntary muscle activity, and determine if the muscle is suitable for transdermal administration of a botulinum toxin. In certain situations, a physician may prefer to use transdermal administration of a botulinum toxin for muscles located near the skin of the patient as opposed to internally located muscles. The physician may also identify potential target sites for transdermal delivery of the botulinum toxin that do not interfere substantially with the patient's overall health and quality of life.

Transdermal administration of proteins, such as insulin, is known and various chemical transport enhancers (such as the skin lipid fluidizer Azone), and diverse methodologies, such as ionotophoresis, have been used to enhance percutaneous penetration of peptides. See e.g. (1) Bodde H. E. et al., Transdermal peptide delivery, Biochem Soc Trans 17(5); 943-5:1989; (2) Verhoef, J. C. et al., Transport of peptide and protein drugs across biological membranes, Eur J. Drug Metab Pharmacokinet 1990 April-June;15(2):83-93, and; (3) Liedtke R. K. et al, Transdermal administration of insulin in type II diabetes. Results of a clinical pilot study; Arneimittelforschung 40(8);884-6:1990 (German). For example, decylmethyl sulfoxide ("DMS") is known to increase the permeation of the skin to thereby facilitate transdermal delivery of peptides. Choi, H-K. et al., Transdermal delivery of bioactive peptides: the effect of n-decylmethyl sulfoxide, pH, and inhibitors on Enkephalin metabolism and transport, Pharm Res 7(11): 1099-1106 (1990). Additionally, ethanol pretreatment of the skin in conjunction with iontophoresis has also been shown to permit transdermal administration of polypeptides. Srinivasan, V. et al., Iontophoresis of polypeptides: effect of ethanol pretreatment of human skin, J Pharm Sci 79(7), July 1990. Thus, a variety of organic solvents as well as surfactants have been used to enhance transdermal delivery of proteins. Sasaki H. et al., Effect of pyrrolidone derivatives on lipid membrane and protein conformation as transdermal penetration enhancer, J Pharmacobio-Dyn., 13; 468-474: 1990.

Furthermore, use of an adhesive patch for transdermal delivery of a therapeutic drug is known. See e.g. Tonnesen, P. et al., A double blind trial of a 16-hour transdermal nicotine patch in smoking cessation, New Eng J Medicine, 325(5); 311-315: August 1991.

The present invention encompasses an adhesive patch (as a botulinum toxin depot) placed onto the surface of the skin of the patient, where the patch comprises a polymeric carrier which can release a therapeutically effective amount of a botulinum toxin onto the skin surface of the patient. Application of a botulinum toxin adhesive, polymeric patch can be preceded by pretreatment of the skin with ethanol wipes or dermal abrasion, and the patch can be used concurrently or in conjunction with a suitable permeation enhancement methodology such as iontophoresis.

The toxin can be presented as a sterile pyrogen-free aqueous solution or dispersion and as a sterile powder for reconstitution into a sterile solution or dispersion.

Where desired, tonicity adjusting agents such as sodium chloride, glycerol and various sugars can be added. Stabilizers such as human serum albumin may also be included. The formulation may be preserved by means of a suitable pharmaceutically acceptable preservative such as a paraben, although preferably it is unpreserved.

It is preferred that the toxin is formulated in unit dosage form, for example it can be provided as a sterile solution in a vial, or as a vial or sachet containing a lyophilised powder for reconstituting a suitable carrier such as water for injection.

In one embodiment the toxin, e.g., botulinum toxin A is formulated in a solution containing saline and pasteurized human serum albumin, which stabilizes the toxin. The solution is sterile filtered (0.2 micron filter), filled into individual vials and then vacuum dried to give a sterile lyophilised powder. In use, the powder can be reconstituted by the addition of sterile unpreserved normal saline (sodium chloride 0.9% for injection).

In another embodiment, the commercially available sterile botulinum toxin type A powder can be incorporated into the polymeric matrix of a suitable carrier using known methodologies, and formed into an adhesive patch for use in conjunction with a skin permeation enhancer such as DMS or Azone.

When the botulinum toxin is administered to juvenile patients, administration of the botulinum toxin should commence before the child has completed its growing period and fixed myostatic contracture has occurred. The benefits of the present methods can be maximized by administering the botulinum toxin to the child at an early stage in its growing period, for example before the child reaches the age of six.

The dose of toxin administered to the patient will depend upon the severity of the condition, e.g., the number of muscle groups requiring treatment, the age and size of the patient and the potency of the toxin. The potency of the toxin is expressed as a multiple of the $LD_{50}$ value of the mouse, one "unit" of toxin being defined as being the equivalent amount of toxin that kills 50% of a group of mice. The definition currently used in relation to the product marketed by Porton Products Limited. According to this definition, the potency of the botulinum toxin A available from Porton Products Ltd. is such that one nanogram contains 40 mouse units (units).

Typically, the dose administered to the patient will be up to about 1000 units, for example, up to about 500 units, preferably in the range from about 80 to about 460 units per patient per treatment, although smaller or larger doses may be administered in appropriate circumstances. The potency of botulinum toxin, and its long duration of action means that doses will tend to be administered on an infrequent basis. Ultimately, however, both the quantity of toxin administered, and the frequency of its administration will be at the discretion of the physician responsible for the treatment, and will be commensurate with questions of safety and the effects produced by the toxin.

Successful treatment of muscle contractures with transdermal delivery of a botulinum toxin can be determined using routine methods known to persons of ordinary skill in the art. For example, successful treatment can be associated with an improvement of one or more symptoms of the muscle contracture, including reduced muscle tone, reduced pain, and/or reduced deformity and the like. The determination can be made by the patient, a physician or nurse, or a combination thereof.

The invention will now be illustrated in greater detail by reference to the following non-limiting examples which describe the results of clinical studies (Example 1 and Case Studies 1 and 2) with botulinum toxin A:

EXAMPLE 1

The Use of Botulinum Toxin A in the Management Children with Cerebral Palsy

Thirty three children suffering from cerebral palsy, having a mean age of seven years and an age range of two to seventeen years, were selected for participation in a clinical study.

The criteria for inclusion in the study were the presence of dynamic contractures interfering with function, without clinical evidence of fixed myostatic contracture. Before entering the study, all children underwent clinical evaluation, physiotherapist's assessment and parental assessment. All ambulatory patients underwent gait analysis using electrogoniometers. The children entering the study were suffering from spastic tetraplegia, diplegia, hemiplegia or monoplegia.

The hamstrings and/or calf muscles of each patient were injected with a sterile solution containing the botulinum toxin A (obtained from Porton Products Limited, UK). Total patient doses ranged from 80 units to 460 units (one unit being equivalent to the murine $LD_{50}$). Before injecting any muscle group, careful consideration was given to the anatomy of the muscle group, the aim being to inject the area with the highest concentration of neuromuscular junctions. Before injecting the muscle, the position of the needle in the muscle was confirmed by putting the muscle through its range of motion and observing the resultant motion of the needle end. General anesthesia, local anesthesia and sedation were used according to the age of the patient, the number of sites to be injected and the particular needs of the patient.

Following injection, it was noted that the onset of effects was complete within thirty-six to seventy-two hours and lasted from six to eighteen weeks. There were no systemic or local side-effects. All but one patient had some reduction in muscle tone; the one failure occurred early in the study and was probably the result of the toxin dosage administered (75 units) being sub-therapeutic. None of the patients developed extensive local hypotonicity. The majority of children had an improvement in function both subjectively and when measured objectively with gait analysis.

Following injection of the calf muscle groups, an assessment was made of the passive dorsiflexion at the ankle. It was found that the younger children displayed a marked improvement in passive dorsiflexion, but that for children over six years there was little improvement. This was probably due to the dynamic contracture being replaced by a fixed contracture which was unresponsive to any amount of paresis.

Case Study 1

A five year old girl with moderate right hemiplegia underwent gait analysis and, on examination, was found to have dynamic contractures of her calf and hamstrings. Gait analysis recordings of sagittal plan movements (with 95% confidence limits) were made prior to injection and these revealed that throughout the gait cycle, the knee was in excessive flexion. Gait analysis also indicated that she was in equinus throughout the gait cycle.

Following injection, the knee could be extended nearly to neutral during stance and the gait analysis pattern, although still abnormal was much improved. The ankle traces recorded indicated that she was able to dorsiflex her ankle in gait and had developed a normal range of movements.

Gait analysis was also undertaken at four months. At this stage the effects of the toxin has clinically worn off and it was found that the knee flexed to the same extent in swing that it did prior to injection. However, the gain of extension in stance was largely preserved. At the ankle, there was some relapse but there was still a lesser degree of equinus.

Case Study 2

Measurements were made of the maximal extension of the knee in a group of patients who underwent hamstring injection. Prior to injection, they all had some degree of dynamic knee flexion contracture. Four weeks following injection, this showed a highly significant improvement. However, the one patient who was least affected developed recurvatum at the knee following injection. After this, all patients who had a dynamic knee flexion contracture of less than fifteen degrees were excluded from hamstring injection. Only one local side-effect from the treatment was noted and this was a small subcutaneous haematoma which resolved itself in a few days.

EXAMPLE 2

The Treatment of the Hereditary Spastic Mouse with Botulinum Toxin A

In cerebral palsy there is frequently a failure of muscle growth leading to fixed muscular contracture. This failure has also been demonstrated in the hereditary spastic mouse (Wright J and Rang M The Spastic Mouse and the search for an animal model of spasticity in human beings) Clin. Orthop. 1990, 253, 12-19.

A study has been carried out to ascertain the effect of Botulinum Toxin A on the growth of longitudinal muscle in the spastic mouse compared with normal siblings. Groups of spastic mice at six days old had one calf muscle injected with either 1.2 units of Botulinum Toxin A or normal saline.

The mice were sacrificed at maturity and the hind limbs dissected to allow measurement of the muscle and bones.

In the control group, the spastic mice had a 13% failure of longitudinal muscle growth compared with their normal siblings. However, the muscles of the spastic mice injected with botulinum had growth identical to that of their normal siblings. There was no difference in growth between normal mice injected with saline or botulinum.

It can be concluded that the injection of intramuscular botulinum toxin during the growth period of the hereditary spastic mouse allows normal longitudinal muscle growth to take place and it is believed that this finding may have significance in the management of cerebral palsy.

EXAMPLE 3

Transdermal Administration of a Botulinum Toxin

A five year old boy with moderate right hemiplegia can undergo gait analysis and, on examination, be found to have dynamic contractures of his calf and hamstrings. Gait analysis recordings of sagittal plan movements (with 95% confidence limits) can be made prior to patch application and can reveal that throughout the gait cycle, the knee is in excessive flexion. Gait analysis can also indicate that he is in equinus throughout the gait cycle.

Following ethanol pretreatment of the skin, an adhesive patch containing DMS admixed with botulinum toxin type A can be applied to the skin above the afflicted muscle region. Within one to two weeks subsequent to patch application, the knee can be extended nearly to neutral during stance and the gait analysis pattern, although still abnormal is much improved. Ankle trace records can indicate that he is able to dorsiflex his ankle in gait and has developed a normal range of movements.

Gait analysis can also be undertaken at four months. At this stage the effects of the toxin are expected to have clinically worn off and it can be found that the knee flexes to the same extent in swing that it did prior to application of the toxin patch. However, the gain of extension in stance can be largely preserved. At the ankle, there can be some relapse but there can still be a lesser degree of equinus. This example shows that transdermal administration of a botulinum toxin can be used to successfully treat juvenile cerebral palsy.

EXAMPLE 4

Transdermal Administration of Botulinum Toxin to Treat Back Pain

A 48 year old male presents with severe back pain on the left side of his body. An evaluation of the patient's posture and work habits can indicate that the patient maintains an undesirable posture while working during most of the day since the patient is often sitting at a desk working on a computer. A conclusion can be made that the patient's poor posture is causing an imbalance in muscle activity near the spine. Massage therapy can be helpful in relieving some of the discomfort; however, the relief is short lived. The physician can conclude that the patient is suffering from muscle contracture which is causing his back pain.

The patient receives an ethanol pretreatment at two regions of the skin on the left side of the spine. An adhesive patch containing DMS admixed with botulinum toxin type A can be applied to the skin at each of the regions pretreated with ethanol. Within one to two weeks subsequent to patch application, a report from the patient indicating that his back pain is reduced compared to the pain experienced prior to botulinum toxin treatment confirms that the transdermal administration of the botulinum toxin type A is successful. The patient can begin to work and function with reduced pain and can begin a physical therapy regime to attempt to correct his poor posture.

EXAMPLE 5

Transdermal Administration of Botulinum Toxin to Treat Ischemic Contracture

A 11 year old male child presents with a fractured elbow. The injury is associated with increased swelling and contracting of forearm muscles, presumably due to a decreased blood flow in the forearm. A physician can prescribe the use of a botulinum toxin transdermal delivery system to reduce muscle contracture of the fingers, hand, wrist, and/or forearm.

An adhesive patch containing a therapeutically effective amount of botulinum toxin type A can be placed at a region near the fracture. After about three days, a decrease in swelling can be observed. Administration of the botulinum toxin can be associated with reduced forearm muscle activity. After about four months, examination of the patient's fingers, hand, wrist and forearm can reveal that the patient does not experience contracture resulting from the injury and ischemia.

As described herein, is has been shown that a Clostridial neurotoxin, such as a biologically active botulinum toxin, can be administered to a patient to treat a contracture of a patient. For example, a botulinum toxin type A can be transdermally administered to treat a muscle contracture, including dynamic and static muscle contractures. In certain embodiments, a botulinum toxin type A can be transdermally administered to treat a muscle contracture associated with cerebral palsy. In other embodiments, a botulinum toxin type A can be transdermally administered to treat a muscle contracture associated with back pain. In yet further embodiments, a botulinum toxin type A can be transdermally administered to treat a muscle contracture associated with an injury and/or reduced blood flow. Transdermal administration of a botulinum toxin can reduce persistent and involuntary muscle shortening associated with a variety of conditions without requiring a needle injection into intramuscular tissue.

The invention has been illustrated by reference to botulinum toxin A but it should be understood that the invention is not limited to the use of this toxin. For example, other botulinum toxins may be employed. Moreover, other presynaptic neurotoxins (e.g., of bacterial origin) which act in a manner similar to botulinum toxin may also be used. Also, synthetic analogues of the botulinum toxins may be envisaged wherein the 50 kD chain and/or the 100 kD chain are subjected to amino acid insertions, deletions and/or substitutions and, provided that such analogues retain the general type of activity exhibited by Botulinum toxin A, their use in the manner described hereinbefore is embraced by the present invention. The invention is also considered to embrace the use of substances structurally dissimilar to Botulinum toxin A, provided that such substances possess a prolonged ability to inhibit or block release of the synaptic vesicles containing acetylcholine.

Any feature or combination of features described herein are included within the scope of the present invention provided that the features included in any such combination are not mutually inconsistent as will be apparent from the context, this specification, and the knowledge of one of ordinary skill in the art. In addition, any feature or combination of features may be specifically excluded from any embodiment of the present invention.

Accordingly, the spirit and scope of the following claims should not be limited to the descriptions of the preferred embodiments set forth above.

All references, articles, patents, applications and publications set forth above are incorporated herein by reference in their entireties.

I claim:

1. A method for treating a muscle contracture of a patient, the method comprising the step of transdermal administration of a botulinum toxin type A to a muscle contracture patient, thereby treating the muscle contracture.

2. The method of claim 1, wherein the transdermal administration step is carried out by contacting a skin surface of the patient with a botulinum toxin depot which can release the botulinum toxin type A for absorption through the skin of the patient.

3. The method of claim 2, wherein the botulinum toxin depot is an adhesive patch which comprises a polymeric carrier for the botulinum toxin type A.

4. The method of claim 1 wherein the botulinum toxin type A is transdermally administered into a spastic muscle of the patient.

5. The method of claim 1 wherein the botulinum toxin type A is transdermally administered into a calf muscle or hamstring of the patient.

6. The method of claim 1, wherein the botulinum toxin type A is transdermally administered to the patient to treat a dynamic muscle contracture.

7. A method of treating a muscle contracture, the method comprising the step of transdermal administration of a therapeutically effective amount of a botulinum toxin type A to a muscle contracture patient by contacting a skin surface of the patient with a botulinum toxin type A depot comprising a polymeric carrier which carrier can release the botulinum toxin type A for absorption through the skin surface of the patient, thereby treating the muscle contracture.

8. The method of claim 7, further comprising the step of pretreatment of the skin with a skin permeation enhancer prior to contacting the skin surface of the patient with the botulinum toxin type A depot.

9. The method of claim 8, further comprising the step of iontophoresis of the skin after the pretreatment step to thereby further enhance transdermal delivery of the botulinum toxin.

10. The method of claim 7, wherein the muscle contracture is a dynamic muscle contracture.

11. A method of treating a muscle contracture, the method comprising the steps of: (a) pretreatment of a skin surface of a patient having a muscle contracture with a skin permeation enhancer; (b) transdermal administration of a therapeutically effective amount of a botulinum toxin type A to the muscle contracture patient by contacting the skin surface of the patient with a botulinum toxin type A depot comprising a polymeric carrier which carrier can release the botulinum toxin type A for absorption through the skin surface of the patient, and; (c) iontophoresis of the skin to further enhance transdermal delivery of the botulinum toxin, thereby treating the muscle contracture.

12. The method of claim 11, wherein the muscle contracture is a dynamic muscle contracture.

* * * * *

UNITED STATES PATENT AND TRADEMARK OFFICE
CERTIFICATE OF CORRECTION

PATENT NO.        : 7,384,918 B2
APPLICATION NO.   : 11/209304
DATED             : June 10, 2008
INVENTOR(S)       : Graham It is certified that error appears in the above-identified patent and that said Letters Patent is hereby corrected as shown below:

On the title page, item (56), under "Other Publications", in column 2, line 40, delete "admnistration" and insert -- administration --, therefor.

On page 2, item (56), under "Other Publications", in column 1, line 2, delete "Hpertension" and insert -- Hypertension --, therefor.

On page 2, item (56), under "Other Publications", in column 2, line 8, delete "Orthrop." and insert -- Orthop. --, therefor.

In column 3, line 38, before "treated" delete "be".

Signed and Sealed this

Fifth Day of August, 2008

JON W. DUDAS
*Director of the United States Patent and Trademark Office*